United States Patent [19]

Newman

[11] Patent Number: 4,824,250
[45] Date of Patent: Apr. 25, 1989

[54] NON-DESTRUCTIVE TESTING BY LASER SCANNING

[76] Inventor: John W. Newman, 601 Maplewood Ave., Wayne, Pa. 19087

[21] Appl. No.: 191,744

[22] Filed: May 5, 1988

Related U.S. Application Data

[63] Continuation of Ser. No. 931,067, Nov. 17, 1986, abandoned.

[51] Int. Cl.$^4$ ............................................. G01N 29/04
[52] U.S. Cl. ...................................... 356/345; 73/588; 73/657
[58] Field of Search ................. 356/32, 35.5, 237, 345; 250/562, 563, 572; 73/577, 578, 588, 598, 655, 657

[56] References Cited

U.S. PATENT DOCUMENTS

| 3,563,652 | 2/1971 | Powell. |
| 3,604,253 | 9/1971 | Kersch. |
| 3,702,737 | 11/1972 | Mottier. |
| 3,879,988 | 4/1975 | Jacobs. |
| 3,900,265 | 8/1975 | Merlen. |
| 3,911,733 | 10/1975 | Bhuta. |
| 3,920,970 | 11/1975 | Slaker. |
| 4,465,371 | 8/1984 | Pernick. |
| 4,508,450 | 4/1985 | Ohshima. |
| 4,567,769 | 2/1986 | Barkhoudarian. |
| 4,641,527 | 2/1987 | Hiroi et al. ........................ 73/588 X |

Primary Examiner—Eugene R. LaRoche
Assistant Examiner—Robert J. Pascal
Attorney, Agent, or Firm—William H. Eilberg

[57] ABSTRACT

The invention provides a method and apparatus for non-destructive testing of bonded structures, such as laminated or composite materials. A beam of coherent light is directed successively onto each point of the object. The reflected beam creates a speckle pattern. The pattern is observed once while the object is stationary and once while the object is mechanically excited. If the point being observed is free of defects, the speckle pattern will be substantially unaffected by the vibration of the excited object. If the point is defective, vibration will blur the speckle pattern. The entire object is scanned, point by point, and the results of the comparison of the speckle patterns obtained for each point are stored and displayed. In another embodiment, the object is made to vibrate continuously, and the apparatus determines whether the speckle pattern is sharp or blurred, for each point being scanned. The sharpness of the speckle pattern can be inferred from the measured intensity of the speckle pattern, or it can be calculated directly by a suitable algorithm. In general, if the detector has a nonlinear response characteristic, the total intensity of the speckle pattern will be lower when the pattern is blurred, and higher when the pattern is sharp. A low intensity therefore indicates that the point on the object is defective. As in the first embodiment, the results of the analysis are stored in a computer memory and displayed on a video monitor.

31 Claims, 7 Drawing Sheets

NON-DESTRUCTIVE TESTING BY LASER SCANNING

This application is a continuation of application Ser. No. 931,067, filed Nov. 17, 1986 now abandoned.

BACKGROUND OF THE INVENTION

This invention relates to the field of non-destructive testing. In particular, the invention provides a method and apparatus which scans a test object with a laser beam to detect defects in the object.

Laser beams have been used, in the prior art, to test objects for defects. One example of non-destructive testing by laser techniques is shown in U.S. Pat. No. 4,408,881. The cited patent shows a system which creates a time-averaged hologram of the object, while the object is made to vibrate at a plurality of frequencies which are uniformly distributed over a preset range. The holographic image of the test object contains interference fringes in areas where there is a defect.

Another example of the use of coherent light for non-destructive testing is given in U.S. Pat. No. 3,604,253. The apparatus disclosed in the latter patent directs a laser beam through a lens, which projects the beam onto the entire object. The object is made to vibrate, and the pattern of light reflected from the object is analyzed. As the frequency and intensity of vibration are varied, changes appear in the pattern, indicating defects in the object.

U.S. Pat. No. 3,900,265 shows another system for detection of flaws in an object. The latter patent shows a device which scans a test object with a laser beam. The intensity of the reflected laser light is analyzed to produce an indication of flaws in the object. The patent discloses improved circuitry for accomplishing the scanning, and for prevention of errors in interpreting the results of the test.

Still another example of a device which scans an object with a laser beam is shown in U.S. Pat. No. 4,508,450. The patent discloses a directed laser which scans the surface of a flat object in a spiral pattern. The reflected light is received by a photodetector, and is compared with a reference signal to give information about defects in the object. The results of the test are displayed on a video monitor.

In U.S. Pat. No. 4,465,371, the distribution pattern of laser light reflected from a test object is examined. Comparison of this pattern with the known pattern of an unflawed object shows whether the object is defective.

The present invention provides another type of system, which is especially useful in detecting flaws in bonded structures, such as laminated materials and composites. The invention has the sensitivity of holography, but does not employ a holographic technique. Instead, the system examines the speckle pattern which results from illuminating a point on the object with coherent light. If there is a defect at a particular point, the speckle pattern obtained from that point will become blurred when the object is made to vibrate. The system of the present invention analyzes the speckle pattern obtained from each point on the object, and thereby determines the location of any defects. A more detailed discussion of the theory of operation of the invention will be presented below.

The apparatus of the present invention produces an image of the object without using holography. In particular, the invention does not employ a reference beam and an object beam, as is required in holography. Moreover, the invention records its results electronically, and not with a photographic process. Thus, the invention eliminates the need for the chemicals used in photographic development. Instead, the results of the analysis are stored in a computer for further review, and can be displayed graphically, on a video monitor. The system is programmed to display a false-color image of the object, which clearly shows the location of defects.

The apparatus also enjoys other important advantages. Unlike a holographic apparatus, it does not require a vibration isolation system. It also does not require any prior knowledge of the surface of the test object; there is no need for a detailed "reference" or "signature" signal, as is needed in some of the above-cited prior art. The invention also eliminates the need for many optical components such as lenses, beam splitters, and the like. Furthermore, because the apparatus scans only one point on the object at a time, it operates with a laser or relatively low power output.

SUMMARY OF THE INVENTION

In one embodiment of the present invention, the object to be examined is held within a fixture. A beam of laser light is successively directed onto each point on the object. A photodetector array, or equivalent device, receives the reflected laser light. The reflected light forms a speckle pattern. While the light is directed towards a given point on the object, the object is made to vibrate. The vibrations are preferably induced by a white noise generator and a piezoelectric transducer. The speckle pattern is detected and recorded in a computer memory, both while the object is vibrating and while it is stationary.

If there is no defect at the point being examined, and if the amplitude of vibration is less than about one-half the wavelength of the incident laser light, then the speckle pattern will be substantially unaffected by the vibration of the object. But if there is a defect at that point, vibration of the object will cause the pattern to become blurred. The system compares the speckle patterns obtained for the vibratory and non-vibratory states. By repeating this comparison for each point on the object, the system determines where the defects are located. The results of the analysis are preferably displayed on a video monitor.

The test object can be perturbed by means other than vibration. If the object is not too rigid, it can be moved by application of heat, changes in air pressure, or electromagnetic energy. If the point on the object is defective, the speckle pattern will not become blurred, but will simply shift, and this shift can be observed.

The entire system is preferably controlled by a computer which coordinates the positioning of the laser beam on the object, and which turns the perturbing mechanism on and off. The computer also stores information concerning each observed speckle pattern, for each point on the object, so that these values can be compared and the results displayed. Also, where the system is used to study large numbers of identical objects, the computer can generate histograms, and other displays of statistical data, giving graphic information about the incidence of defects.

In another embodiment, the object is continuously vibrated while being scanned with coherent light. At points at which there is a defect, the resulting speckle pattern will be blurred. The reflected light is received, as before, by a suitable photodetector array, and a computer examines the condition of the speckle pattern. If the photodetector has a nonlinear response characteristic, the total intensity of the speckle pattern will be greater if the pattern is sharp, than if it is blurred. If the photodetector has a linear response, the computer can be programmed to determine directly the sharpness of the pattern, through an algorithm which examines the transitions from light to dark on the pattern. In either case, the results are displayed and stored, as before. This second embodiment enjoys the advantage that the vibrating means is not turned on and off repeatedly. Thus, it is not necessary to wait for the vibrating object to come to rest, at each point being examined. The second embodiment therefore enables the object to be scanned more rapidly.

It is therefore an object of the invention to provide a system for non-destructive testing, using a laser scanning technique.

It is another object of the invention to provide a system, as described above, the system being suitable for detection of defects in bonded materials.

It is another object to provide a system as described above, wherein the system is non-holographic, but wherein the apparatus has the sensitivity of holography.

It is another object to provide a system as described above, wherein the system provides a digitally generated display of the object, indicating the positions of all defects therein.

It is another object to enhance the speed with which bonded materials can be tested by non-destructive techniques.

It is another object to provide a method and apparatus which can test for defects in a variety of bonded structures.

It is another object to provide a method of non-destructive testing, using laser techniques.

It is another object to provide a method as described above, the method being non-holographic, and the method being capable of results equal or superior to those of holography.

It is another object to provide a system for non-destructive testing, wherein the object to be tested is continuously vibrated.

It is another object to provide an analog system for non-destructive testing, wherein an analog signal can be digitally processed to yield information about the location of defects in an object.

Other objects and advantages of the invention will be apparent to those skilled in the art, from a reading of the following brief description of the drawings, the detailed description of the invention, and the appended claims.

DETAILED DESCRIPTION OF THE INVENTION

It is helpful first to review the theory which underlies the present invention. The invention relies on the basic fact that when a beam of coherent light is directed at an irregular surface, a "speckle pattern" is observed. Examples of such speckle patterns are shown in the photographs of FIGS. 2-5.

Figure 2:
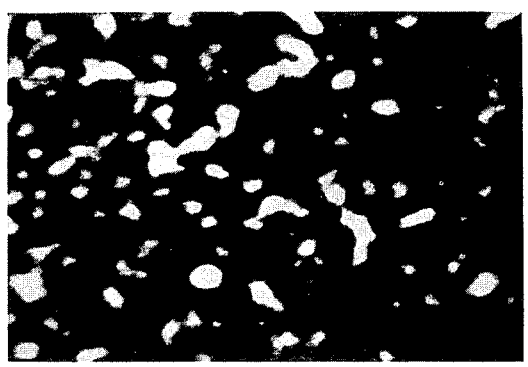
FIG. 2 is a photograph of a speckle pattern, generated by directing a laser beam at point A of FIG. 1, without causing the object to vibrate.

The speckle pattern of FIG. 2 is observed for any surface which has irregularities larger than the wavelength of the incident laser light. The incident light impinges on adjacent peaks and valleys on the surface at slightly differing moments. Thus, the reflected light includes a plurality of beams having slightly differing phases. The speckle pattern is the result of the interference of these reflected beams. The speckle pattern will be observed only if the incident beam is coherent. If ordinary light were used, the distribution of phases would be so random that the phase shifts due to the peaks and valleys would not be observable.

It must be emphasized that the speckle pattern, such as that shown in FIG. 2, is the pattern resulting from directing a laser beam at a single point on the object. The pattern of FIG. 2 is not a representation of the entire object.

The speckle pattern may be observed by projecting it onto a screen, or onto any other suitable detector. As the screen or detector is moved away from the object, the speckle pattern grows larger, but still retains the same shape. Also, as the width of the incident laser beam is increased, increasing the size of the illuminated region on the object, the speckles become smaller. As the laser beam becomes more focused, the speckles become larger. If the width of the beam is too large, there will be a very large number of phase-shifted reflected beams, all of which interfere with each other, destroying the speckle pattern, and producing a uniform reflection of the laser light.

Vibration of the object can cause changes in the speckle pattern. If the amplitude of vibration is greater than about one-half the wavelength of the incident laser light, the speckle pattern will become blurred. The incident beam will be, in effect, reflected from a moving object, and the reflections will occur while the object is at varying distances from the observer. If the object is moved, but not vibrated, the speckle pattern will shift, but will not become blurred.

If the amplitude of vibration of the object is less than about one-half the wavelength of the incident light, the speckle pattern will remain substantially unchanged. In effect, the incident light "sees" a substantially stationary surface.

Consider what happens when a bonded object is made to vibrate. If the object is not defective, it will vibtrate only at certain characteristic frequencies, and with certain characteristic mode shapes. But if the object is defective, i.e. if the bonded material has become delaminated, the object will vibrate along many more modes. Indeed, if the incident acoustic wave energy, which generates the vibration, is distributed over a range of frequencies, the defective material is virtually certain to vibrate in resonance, at least at one of these frequencies. The amplitude of the resonant vibration, at the site of a defect, is greater than that of the vibrational amplitude of the major portion of the test object.

From the above discussion, it follows that if an object to be tested is subjected to a low level of vibration, such that the amplitude of vibration is less than about one-half of one wavelength of the incident light beam, and if the frequencies of the input vibrations are sufficiently distributed over the spectrum, then the amplitude of induced vibration of the object will exceed the one-half wavelength level only at those points where there is a defect. When these defective points are scanned by a laser beam, the resulting speckle patterns will be blurred. The present invention detects defects in the object by detecting blurring of the speckle pattern when the object is in vibration.

The present invention detects defects of the type wherein two or more components, intended to be firmly bound together, have become separated. Thus, the invention is applicable to the large class of materials known as "bonded structures", including laminated and composite materials, among others. The invention will detect any defect wherein a defective portion of the object can move, however slightly, relative to the remainder of the object.

Figure 1:
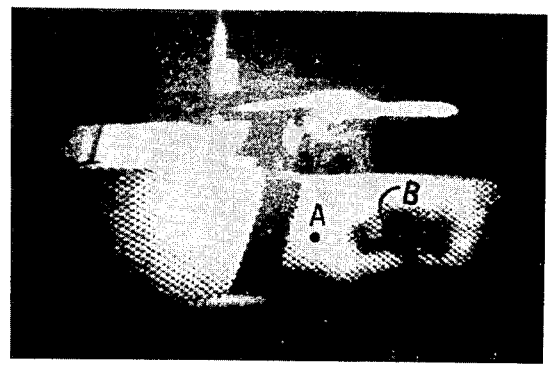
FIG. 1 is a photograph of a hologram showing an object having a defective portion.
Figure 3:
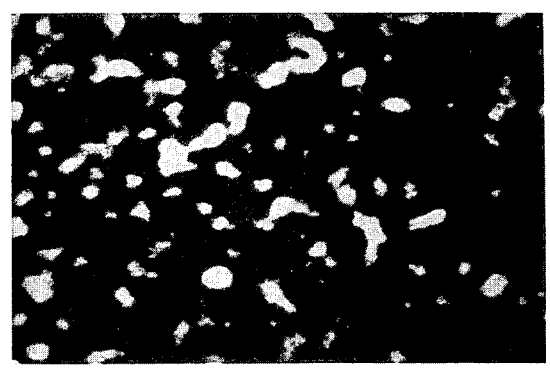
FIG. 3 is a photograph of the speckle pattern of FIG. 2, while the object is vibrating.
Figure 4:
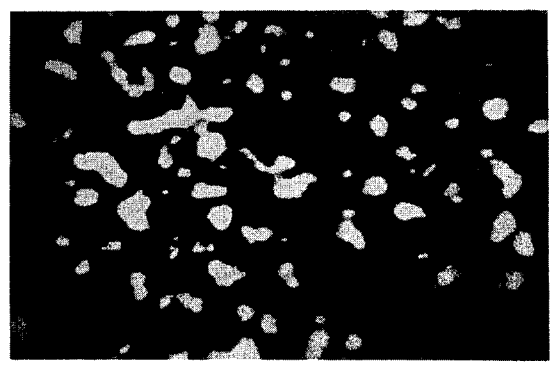
FIG. 4 is a photograph of a speckle pattern generated by directing a laser beam at point B on FIG. 1, without vibration.
Figure 5:
FIG. 5 is a photograph of the speckle pattern of FIG. 4, while the object is vibrating.

The photographs of FIGS. 1-5 illustrate the principles discussed above. The speckle patterns of FIGS. 2-5 were obtained by directing a laser beam at specific points on the test object shown in FIG. 1. FIG. 1 is a photograph of a hologram of a test object. The object contains defect-free portions, which appear as light areas, and defective portions, which appear dark. Point A, in FIG. 1, is located within a light area, and represents a defect-free point on the object. Point B represents a defective point, and is located within the dark patch, to the right of Point A. FIGS. 2 and 3 show the speckle patterns generated from Point A. In FIG. 2, the object was not vibrating; in FIG. 3, the object was vibrating. Similarly, FIGS. 4 and 5 show the speckle patterns generated from Point B. In FIG. 4, the object was not vibrating; in FIG. 5, the object was vibrating.

In the prior art, the condition of the test object was determined by making a hologram, as shown in FIG. 1, and examining the hologram for dark areas. The dark areas represent the defective portions of the object. The present invention avoids the need for making a hologram.

Figure 6:
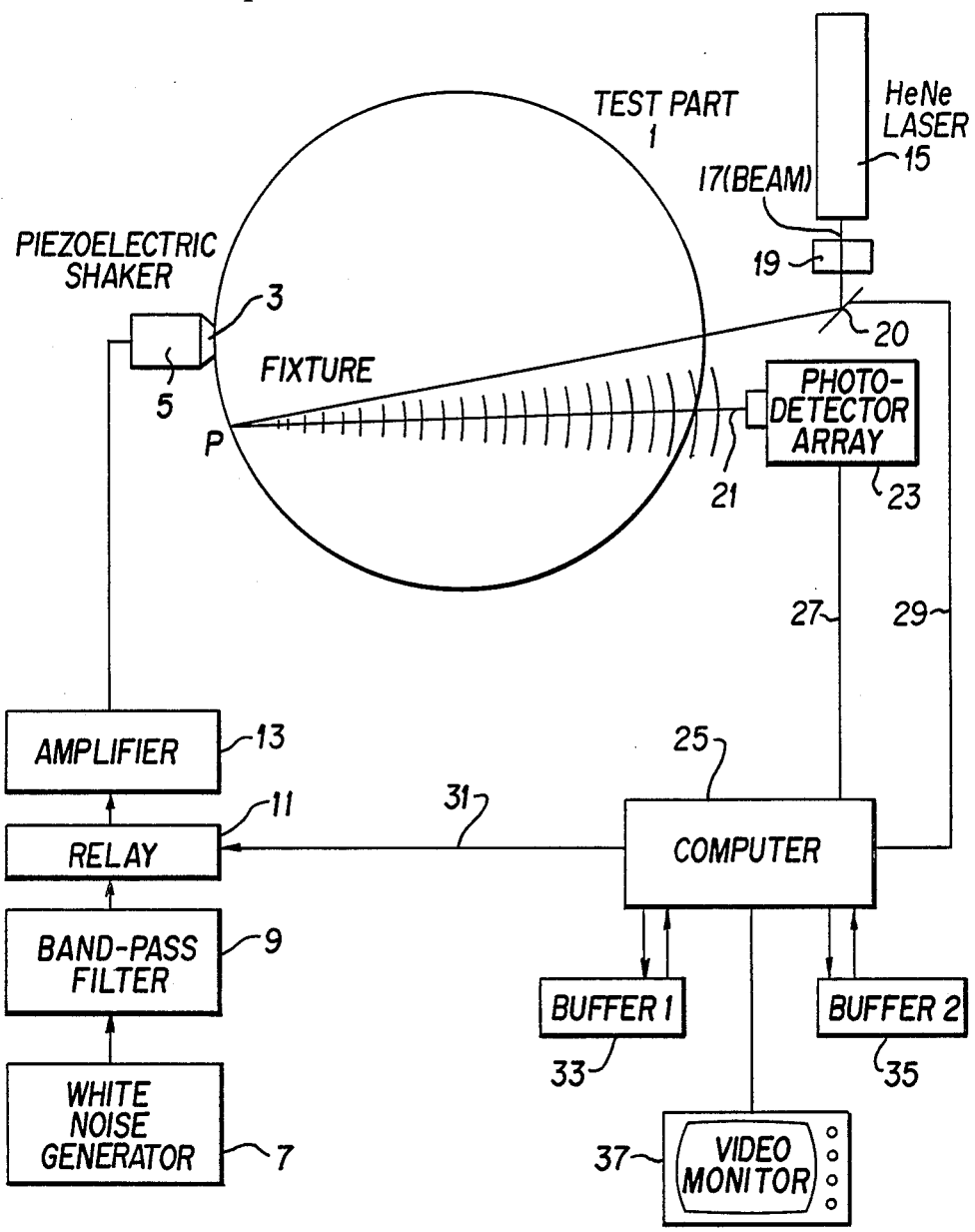
FIG. 6 is a schematic diagram of a first embodiment of the invention, wherein the test object is scanned both with and without vibration.

A schematic diagram of one embodiment of the present invention is shown in FIG. 6. Test object 1 is held by fixture 3. Fixture 3 is connected to piezoelectric shaker 5, which induces vibrations in object 1. Noise generator 7 produces an electrical "noise" signal, preferably of the type known as "white noise", i.e. a signal having frequency components distributed across a wide bandwidth. The signal from generator 7 is passed through band pass filter 9, through relay 11, and to amplifier 13. The shaker 5 converts the electrical noise signal into mechanical vibrations. The relay is preferably controlled by a computer, as described below.

It is understood that the excitation can be induced in the object by other means. The arrangement shown is only an example, and is not intended to limit the invention.

Laser 15, which can be a helium-neon laser, or other suitable type, generates beam 17 of coherent light. The beam is directed, by mirrors 19 and 20, towards a point P on object 1. It is preferable to use two separate mirrors for moving the beam in the horizontal and vertical directions. However, it is possible to use a single mirror which is mounted for rotation with two degrees of freedom. Both alternatives are intended to be within the scope of the invention.

Reflected beam 21 is detected by photo-diode detector array 23. The photo-diode array could be a two-dimensional array, or it could be a linear array. The output of detector 23 is, in general, a speckle pattern of the type discussed above. The signals from detector 23 are sampled by computer 25, through line 27.

The invention is not limited to use of a photo-diode array; other equivalent detection means can also be used. For example, one could use a video camera without a lens. It is necessary only to provide a plurality of light-sensitive elements.

Note that the term "linear array" is used to denote the one-dimensional nature of the array; the term "linear" is used elsewhere in this description to denote the response characteristic of the detector.

Computer 25 is connected to control lines 29 and 31. The computer controls the positions of the mirrors 19 and 20. It also controls relay 11, thereby controlling the vibration of the test object. The computer is also shown connected to buffers 33 and 35. In practice, the buffers can be part of the computer, or they can be separate circuits housed within the same frame as the computer.

Buffer 33 stores the sampled signal data from the photo-diode array, for a given point P, when the test object is not vibrating. Buffer 35 stores the sampled signal data from the photo-diode array when the test object is vibrating. The computer is programmed to compare the contents of each address in buffer 33 with the contents of the corresponding address in buffer 35, to determine whether the speckle pattern has been changed by vibration of the object. The results of the comparison are displayed on video monitor 37.

The computer is programmed to examine every point on the test object, or, alternatively, every point of a selected region of the object. A distinction should be drawn between the scanning of the test object, and the "scanning" of the speckle patterns. Each speckle pattern results from one point only. The system generates two speckle patterns for each point. Thus, the examination of each segment of the speckle patterns should not be confused with the examination of each point on the object.

The operation of the system can now be described. The system operates in cycles, each cycle representing the examination of a particular point on the test object. At the beginning of a cycle, relay 11 is open, and the object does not vibrate. The computer selects the next point to be examined, and issues a control signal which moves mirrors 19 and 20. Laser beam 17 is directed onto the desired point.

The resulting speckle pattern is detected by photo-diode array 23, and is stored, by the computer, in buffer 33. The computer then issues a signal to close relay 11, connecting the vibration generator to the test object. The object begins to vibrate, and the computer directs the output of array 23 into buffer 35.

The computer then compares the contents of each address in buffer 33 with the contents of the corresponding address of buffer 35. The result of the comparison is stored, in the computer memory, for display on monitor 37.

The computer then opens relay 11, disabling the vibration generator, and the cycle is complete. The next cycle begins when the computer selects the next point on the object to be scanned, and directs the laser beam onto that point, by repositioning mirrors 19 and 20. Each cycle may take up to 0.1 seconds, or less, depending mainly on the speed with which the mirrors can be moved, and on the time required for the object to stop vibrating. In practice, the next test cycle may begin prior to the complete cessation of vibration of the object. The actual time during which each point on the object is illuminated by the laser light is at least an order of magnitude less than the length of the test cycle, and is typically no more than about 0.0001 seconds.

In theory, if there is no defect in the object, the speckle pattern will be unchanged when the object is made to vibrate. Thus, in theory, if the object is defect-free, the contents of buffers 33 and 35 should be identical. In practice, noise and signal leakage will produce differences between the outputs of array 23, before and during vibration, even for a defect-free object. It is thus necessary that the computer be programmed to allow for these effects. The computer can therefore be programmed to determined whether the sum of the absolute values of the differences between corresponding addresses in the buffers is less than a predetermined value. If the sum is less than that value, the object must be free of defects at the point being examined, and the computer can be programmed to insert, say, a white pixel on the appropriate point of a raster on monitor 37. If the sum is less than the threshold value, then the object must have a defect at that point, and the computer can insert a black (or other colored) pixel at the appropriate point on the raster.

The display can also contain more than two colors. For example, the colors green, blue, and red could signify degrees of defectiveness. One can establish a gradation of defective conditions, represented by the integers $N_1$ and $N_2$. If the sum of the absolute differences of the intensities of each point of the speckle patterns, for a particular point P, is less than $N_1$, then the system would generate a green pixel on the appropriate point of the display. If the sum is greater than or equal to $N_1$ but less than $N_2$, the system would generate a blue pixel. If the sum is greater than or equal to $N_2$, then the system would display a red pixel. The green areas on the display would indicate areas which are free of defects. The red areas would be defective regions. The blue areas would be regions of intermediate quality. Other color schemes could, of course, be chosen, and more gradations of quality could be added. In this way, the system can provide a very detailed view of the condition of the test object.

The power input to the piezoelectric shaker, or other vibration generator, must be adjusted so that the amplitude of vibration is neither too small nor too large. If the amplitude of the input signal is too small, then even when the test object is defective, the induced vibrations will not have an amplitude sufficient to exceed the level of about one-half the wavelength of the incident light. In this case, there will be no significant change in the speckle pattern. And if the amplitude of the input signal is too large, then every point on the object will vibrate with a large amplitude, and the apparatus will falsely indicate that the entire object is defective.

The electrical noise generator is specifically chosen to be a "white noise" generator. By supplying a signal having frequency components distributed over a wide band, the apparatus is virtually certain to excite many resonant modes of vibration for defective areas on the object.

As stated above, the size of the speckle pattern varies with the distance of the detector from the object. As the detector is moved farther away from the object, the pattern grows larger. When the pattern is made larger in this way, its sensitivity to vibration is increased. When all the features of the speckle pattern are bigger, it is easier to detect subtle changes in the pattern. Thus, with the present invention, it is possible to increase the sensitivity of the apparatus by moving the detector away from the object, without changing the amplitude of the input signal.

In practice, the sensitivity of the apparatus can be adjusted in two different ways. One can vary the amplitude of the input signal to the vibration generator, and one can also vary the distance between the photo-diode array and the object. Both of these means of adjustment are independent of each other. The present invention therefore offers flexibility of operation which is not present in the devices of the prior art.

The embodiment described above is not limited to the use of vibration as a means of excitation of the test object. In cases where the test object is not exceedingly rigid, as is true for objects which include very thin metallic pieces or layers of thin films, other means can be used to cause a defective portion to move. For example, the object can be exposed to heat, pressure, a vacuum, or electromagnetic forces. An unbonded area will respond by moving slightly, and this motion causes a shift in the speckle pattern. Unlike the case of mechanical vibration, the speckle pattern, in this case, does not become blurred, but instead shifts from one position to another. The data from the photo-diode array could be analyzed in a manner identical to that described above, since any change in the speckle pattern, whether by blurring or by shifting of position, indicates a defective area.

The choice of the means of perturbing the object (i.e. vibration, heat, pressure, etc.) depends on the rigidity of the object. Vibration is the necessary perturbing means where the object is fairly rigid, and where the other types of stimuli would not be likely to affect the object.

All of the above-cited means of perturbing the test object should be deemed within the scope of the present invention.

The present invention thus has significant advantages when compared with non-destructive testing equipment of the prior art. It is certainly preferable to the holographic methods and devices currently available. Because the system scans only one point of an object at one time, it is not necessary to use a high-powered laser. A relatively inexpensive, reliable, low-powered laser can be used, because its beam will be concentrated on only one point at a time. Moreover, the present invention eliminates the need for a complex optical system, as is required in holography. By contrast, holographic systems need vibration isolation systems, lenses, beam splitters, and other complex optical components.

It is a significant advantage of the present invention that no vibration isolation system is needed. Because a hologram is typically exposed over a period of several seconds, it is always necessary to isolate the test object from stray vibrations. While a hologram is being exposed, no part of the system, including the object, may move more than about one-tenth of the wavelength of the incident light, i.e. a distance of approximately 500 angstroms. Otherwise, the interference pattern, which is the essence of holography, will be degraded or destroyed. But with the present invention, each point of the test object is scanned for a very brief time, of the order of 0.0001 seconds. Since the typical sources of vibration are sound waves in the air and floor, having a frequency of the order of about 1–200 Hz, such waves will have virtually no effect on the present invention, because of the brief time during which each point is exposed to the laser beam.

The present invention also avoids the need for the expensive and messy chemicals used in photographic development. In the present invention, the data are stored digitally in a computer memory. The data can thus be easily retrieved and re-analyzed mathematically.

Although the vibratory embodiment described above works well, it has one disadvantage. The laser beam scans the entire test object, point by point. At each point, it is necessary to record a speckle pattern, both while the object is vibrating and while it is stationary. Thus, the piezoelectric shaker is repeatedly turned on and off. Each time the power is turned off, there is a period, of the order of milliseconds, during which the vibration of the object continues. The vibration decays at an exponential rate until the object comes to rest. Thus, for each cycle of operation, there is a certain "dead time", which limits the speed at which the entire object can be scanned.

Figure 7:
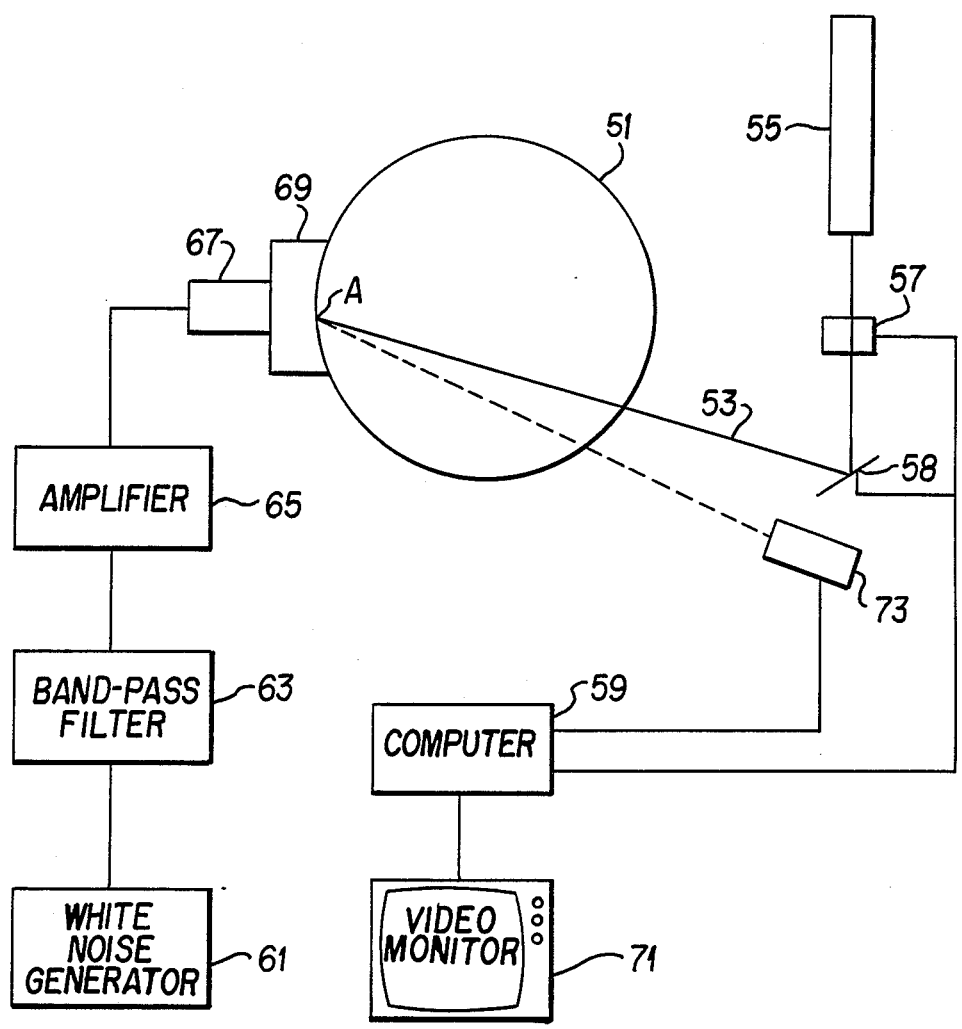
FIG. 7 is a schematic diagram of a second embodiment of the invention, wherein the test object is vibrated continuously.

In the embodiment of the invention shown schematically in FIG. 7, the test object is subjected to continuous vibration, and there is no "dead time". In FIG. 7, object 51 is scanned by laser beam 53, which originates in laser 55. Mirrors 57 and 58 determine the location of the point A onto which the beam is directed. The mirrors are controlled by computer 59. The beam may be moved in discrete steps, along the object, or may be moved with continuous motion. In the latter case, it is necessary that both the photo-diode array and the computer have very short response times.

Vibrational energy comes from white noise generator 61, the output of which is passed through band pass filter 63 and amplifier 65. The signal is applied to piezoelectric shaker 67, which converts the electrical signal to mechanical vibrations. The vibrations are transmitted to object 51 through fixture 69.

The pattern of reflected laser light is received by photo-diode array 73, the output of which is connected to computer 59. The output of the computer is preferably viewed on video monitor 71.

Computer 59 is programmed to determine whether the speckle pattern being received from array 73 is sharp or blurred. One means of making this measurement involves the use of a detector array having a non-linear response characteristic. If the response curve of the detector is non-linear, then sharp points of brightness in the speckle pattern will contribute disproportionately to the total output of the photo-diode array. Thus, the total output of the array will be greater when the speckle pattern is more sharp. Conversely, a blurred pattern has fewer bright points, and the total output of the detector, for this pattern, would be reduced. It is thus a simple matter to measure the total output of the photo-diode array 73, and to compare the measured value with a predetermined threshold. The computer can be programmed to determine whether the output of the array is greater than or less than this predetermined value. The computer can thus generate the appropriate pixel for the video display, and can also store the numerical value of the intensity in its memory. As in the first embodiment, the apparatus can be programmed to display gradations of defective conditions. The computer can be programmed to determine the interval within which the intensity falls, and to generate a colored pixel accordingly.

One can also use two photo-diode arrays, one located farther from the object than the other. The speckle pattern would be larger for the more distant array, and its intensity would be less. But if the pattern is blurred, the output of the more distant array would be even further reduced. This difference in signal level can be measured and converted into a signal for the display.

It is also possible to determine the condition of the speckle pattern by applying an algorithm to evaluate the pattern directly. The computer can determine whether the pattern is sharp or blurred by evaluating each bright spot of the pattern, and by determining whether the transition from light to dark, or vice versa, is steep or gradual.

After analyzing the speckle pattern by any of the techniques described above, or by any equivalent means, the computer generates a signal which determines the color or gray scale of a pixel on monitor 71. As in the first embodiment, the computer can generate one of two possible output values, representing defective and defect-free conditions. In this case, one would need a video monitor capable of displaying playing only black and white images. The computer can be programmed to display pixels having a range of gray scales or color values, which the computer could use to indicate different levels of intensity of the speckle pattern, thereby indicating different levels of defectiveness. When three or more colors are used, the defective areas can be better highlighted.

Both embodiments described above have advantages and disadvantages. As explained above, the scanning can be done more quickly with the second embodiment, because the test object is kept in constant vibration, and there is no need to wait for the object to come to rest. But is the object is relatively complex in shape, it is preferable to use the first embodiment, because the reflectivity of the surface of a complex object varies considerably from point to point. At those points having relatively low reflectivity, the output of the photo-diode array drops significantly, decreasing the signal to noise ratio, and giving an erroneous indication that the points are defective. But the first embodiment, which compares two speckle patterns for the same point, is relatively independent of the changes in reflectivity from one test point to the next.

This invention should not be deemed limited by the description, given above, of the scientific principles of its operation. The observed changes in the speckle patterns, for example, may be due to factors other than those discussed, which are not yet fully understood.

While the invention has been described with respect to the specific embodiments discussed above, it is understood that the invention can be modified in many ways. The algorithms used to evaluate and/or compare speckle patterns can be modified, as suggested above. The particular type of laser, and the means of directing the beam onto a point on the test object can also be varied. The particular type of photodetector can be changed. These and other similar modifications should be deemed within the spirit and scope of the following claims.

What is claimed is:

1. A system for non-destructive testing of an object, comprising:
   (a) means for holding the object,
   (b) means for vibrating the object, the vibrating means being connected to the holding means,
   (c) means for directing a beam of coherent light onto a predetermined point on the object, so as to form a reflection pattern,
   (d) means for detecting the reflection pattern obtained from the object,
   (e) control means, the control means being adapted to energize and de-energize the vibrating means, and to control the beam directing means, wherein successive points on the object can be scanned by the beam, the control means being programmed to energize and de-energize the vibrating means while the beam is directed towards each point on the object, and
   (f) display means for indicating, for each point on the object, the difference between the reflection pattern when the object is vibrating and when the object is stationary.

2. The system of claim 1, wherein the control means is a computer.

3. The system of claim 2, wherein the display means is a video monitor.

4. The system of claim 3, wherein the vibrating means includes a white noise generator and a piezoelectric shaker.

5. The system of claim 4, wherein the detecting means comprises an array of photodiodes.

6. The system of claim 5, wherein the directing means comprises at least one mirror for deflecting the beam.

7. A system for non-destructive testing of an object, comprising:
   (a) means for vibrating the object, the vibrating means being connected to the object,
   (b) means for directing a beam of coherent light onto a predetermined point on the object, so as to form a reflection pattern,
   (c) means for detecting the reflection pattern obtained from the object,
   (d) control means, the control means being adapted to actuate and deactuate the vibrating means, and to control the beam directing means, wherein successive points on the object can be scanned by the beam, the control means being programmed to actuate and deactuate the vibrating means while the beam is directed towards each point on the object, and
   (e) display means for indicating, for each point on the object, the difference between the reflection pattern when the object is vibrating and when the object is not vibrating.

8. A system for non-destructive testing of an object, comprising:
   (a) means for directing a beam of coherent light at a predetermined point on the object,
   (b) means for detecting the intensity of the light reflected from the object,
   (c) means for vibrating the object, the vibrating means comprising means for inducing vibrations having frequency components distributed across a wide bandwidth, and
   (d) means for controlling the directing means and the vibrating means, such that the beam is successively directed onto a plurality of points on the object, and such that the beam is directed towards a particular point both while the object is vibrating and while the object is not vibrating.

9. The system of claim 8, wherein the controlling means is a computer, the computer being programmed to store information obtained from the detecting means when the object is vibrating and when the object is not vibrating.

10. The system of claim 8, wherein the vibrating means includes means for adjusting the amount of vibrational energy imparted to the object.

11. The system of claim 10, wherein the ibrating means includes a white noise generator.

12. The system of claim 8, wherein the detecting means includes an array of photo-diodes.

13. The system of claim 8, further comprising relay means for actuating the vibrating means.

14. A method for non-destructive testing of an object, comprising the steps of:
    (a) directing a beam of coherent light at a point on the object, while the object is not vibrating,
    (b) measuring the intensity of the light reflected from the non-vibrating object,
    (c) directing a beam of coherent light at the same point on the object, while the object is vibrating, the object being made to vibrate by a vibrating means which contacts the object,
    (d) measuring the intensity of the light reflected from the vibrating object,
    (e) comparing the intensity of the light reflected from the object when the object is vibrating and when it is not vibrating, and
    (f) repeating the above steps for each point on the object.

15. The method of claim 14, wherein each of the measuring steps comprises the step of observing a speckle pattern produced by the reflected light.

16. The method of claim 15, wherein the comparing step comprises comparing the intensity of each point on each speckle pattern produced.

17. The method of claim 14, further comprising the step of storing the results of each comparing step in the memory of a computer.

18. The method of claim 14, further comprising the step of displaying the results of each comparing step on a video monitor means.

19. The method of claim 18, wherein the comparing step includes the step of determining the amount by which the intensities of the light differ, and wherein the displaying step comprises the step of displaying a colored pixel corresponding to said amount.

20. A method for non-destructive testing of an object, comprising the steps of:
    (a) directing a beam of coherent light at a point on the object while the object is stationary,
    (b) measuring the intensity of the light reflected from the stationary object,
    (c) vibrating the object, while directing a beam of coherent light at the same point on the object, the vibrating step being performed with a vibrating means which is in contact with the object,
    (d) measuring the intensity of the light reflected from the vibrating object,
    (e) comparing the intensity of the light reflected from the object when the object is vibrating and when it is not vibrating, and
    (f) repeating the above steps for each point on the object.

21. A method for non-destructive testing of an object, comprising the steps of:
   (a) directing a beam of coherent light at a point on the object, while the object is not vibrating,
   (b) measuring the intensity of the light reflected from the non-vibrating object,
   (c) directing a beam of coherent light at the same point on the object, while the object is vibrating, the object being made to vibrate by a vibrating means which contacts the object,
   (d) measuring the intensity of the light reflected from the vibrating object, and
   (e) comparing the intensity of the light reflected from the object when the object is vibrating and when it is not vibrating.

22. The method of claim 21, wherein each of the measuring steps comprises the step of observing a speckle pattern produced by the reflected light.

23. The method of claim 22, wherein the comparing step comprises comparing the intensity of each point on each speckle pattern produced.

24. A method for non-destructive testing of an object, comprising the steps of:
   (a) subjecting the object to continuous vibration, the object being made to vibrate by a vibrating means which contacts the object,
   (b) directing a beam of coherent light onto a point on the vibrating object,
   (c) detecting a speckle pattern formed by the reflection of said beam of coherent light, from each point on the object,
   (d) measuring the sharpness of the speckle pattern, and
   (e) repeating the directing, detecting, and measuring steps for each point on the object.

25. The method of claim 24, wherein the detecting step comprises using a detector array having a nonlinear response characteristic, and wherein the measuring step comprises the step of measuring the intensity of the speckle pattern.

26. The method of claim 24, wherein the measuring step includes the step of displaying a pixel on a video monitor, the color of the pixel corresponding to the level of measured sharpness of the speckle pattern for a given point on the object.

27. A method for non-destructive testing of an object, comprising the steps of:
   (a) subjecting the object to continuous vibration, the object being made to vibrate by a vibrating means which contacts the object,
   (b) directing a beam of coherent light at a point on the vibrating object,
   (c) detecting a speckle pattern formed by the reflection of said beam of coherent light, and
   (d) measuring the sharpness of the speckle pattern.

28. The method of claim 27, wherein the directing, detecting, and measuring steps are performed repeatedly for each point on the object.

29. The method of claim 28, wherein the measuring step comprises the step of determining the intensity of the speckle pattern.

30. The method of claim 28, wherein the measuring step is followed by the step of displaying a pixel on a video monitor, the color of the pixel corresponding to the level of measured sharpness of the speckle pattern for a given point on the object.

31. The method of claim 30, further comprising the step of storing the information on the sharpness of the speckle pattern, for each point on the object, in the memory of a computer.

* * * * *